United States Patent [19]

Lege

[11] Patent Number: 4,571,309

[45] Date of Patent: Feb. 18, 1986

[54] $C_{22}$-CYCLOALIPHATIC TRICARBOXYLIC ACID DERIVED ISETHIONATE ESTERS AND METHOD OF PREPARATION

[75] Inventor: Curtis S. Lege, Ladson, S.C.

[73] Assignee: Westvaco Corporation, New York, N.Y.

[21] Appl. No.: 515,212

[22] Filed: Jul. 20, 1983

[51] Int. Cl.$^4$ .............. C07C 143/90; C11D 1/28
[52] U.S. Cl. .................. 260/400; 560/127; 252/117
[58] Field of Search .............. 260/400; 560/127; 252/117

[56] References Cited

U.S. PATENT DOCUMENTS

| | | | |
|---|---|---|---|
| 1,906,484 | 5/1933 | Nuesslein . | |
| 2,749,315 | 6/1956 | Faier | 252/117 |
| 2,781,321 | 2/1957 | Mayhew et al. | 252/161 |
| 2,894,912 | 7/1959 | Geitz | 252/121 |
| 3,004,049 | 10/1961 | Schenck | 260/400 |
| 3,320,292 | 5/1967 | Cahn et al. | 260/400 |
| 3,383,396 | 5/1968 | Cahn et al. | 260/400 |
| 3,394,155 | 7/1968 | Cahn et al. | 260/400 |
| 3,420,857 | 1/1969 | Holland et al. | 260/400 |
| 3,420,858 | 1/1969 | McCrimlisk | 260/400 |
| 3,429,136 | 2/1969 | Holt et al. | 260/400 X |
| 3,842,119 | 10/1974 | Bills | 260/468 K |
| 3,880,897 | 4/1975 | Landy | 260/400 |
| 4,081,462 | 3/1978 | Powers et al. | 260/501.1 |
| 4,092,259 | 5/1978 | Prince | 252/117 |
| 4,092,260 | 5/1978 | Prince | 252/117 |
| 4,096,082 | 6/1978 | Prince | 252/117 |
| 4,180,470 | 12/1979 | Tokosh et al. | 252/121 |
| 4,405,526 | 9/1983 | Lamberti et al. | 260/400 |
| 4,435,328 | 3/1984 | Lamberti et al. | 260/400 |
| 4,476,055 | 10/1984 | Du Vernet | 260/400 |

FOREIGN PATENT DOCUMENTS 1059984 2/1967 United Kingdom .

OTHER PUBLICATIONS

*Chemical Abstracts*, "Ester-Like Wetting, Foaming and Dispersing Agents" (U.S. 1,881,172), vol. 27 (Jan. 10-Apr. 20, 1933), p. 575.

*Official Gazette*, vol. 933, No. 4 (Apr. 22, 1975), p. 1747, U.S. Pat. No. 3,879,309.

Primary Examiner—Helen M. S. Sneed
Attorney, Agent, or Firm—Terry B. McDaniel; Richard L. Schmalz

[57] ABSTRACT

Novel anionic emulsifiers are disclosed as well as their preparation by reacting an ammonium or substituted ammonium methyl isethionate alcohol with $C_{22}$-cycloaliphatic tricarboxylic acid of the formula

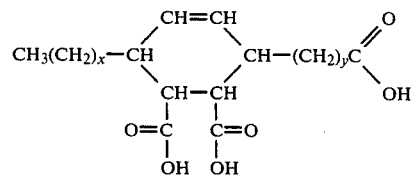

where x and y are integers from 3 to 9, and x and y together equal 12. The oil-soluble emulsifiers are effective in emulsifiable concentrates used in agricultural chemical delivery systems.

12 Claims, No Drawings

$C_{22}$-CYCLOALIPHATIC TRICARBOXYLIC ACID DERIVED ISETHIONATE ESTERS AND METHOD OF PREPARATION

BACKGROUND OF THE INVENTION (1) Field of the Invention

This invention relates to $C_{22}$-cycloaliphatic tricarboxylic acid based isethionate esters and their use as oil-soluble anionic emulsifier intermediates for emulsifiable concentrates used in agricultural chemical delivery systems. The invention also relates to the method of producing the emulsifiers by the reaction between $C_{22}$-cycloaliphatic tricarboxylic acid and the adduct produced from reacting propylene oxide and ammonium bisulfite.

(2) Description of the Prior Art

2-Hydroxyethane sulfonic acid is also known as isethionic acid and its salts are known as isethionates. A history of the development of methods for synthesizing isethionates is provided in British Pat. No. 1,059,984 which is incorporated by reference herein. The patent also discloses the method of preparing metal salts of 2-hydroxyalkane sulfonic acids which comprises reacting ammonia or a volatile amine with sulfur dioxide to form a bisulfite which is then reacted with an alkylene oxide.

U.S. Pat. No. 1,881,172 teaches ester-ethanesulfonic acids which possess soap-like wetting and emulsifying properties. The patent teaches, generally, causing hydroxylated or halogenated derivatives of ethanesulfonic acid to react with the higher fatty acids or their suitable derivatives.

U.S. Pat. Nos. 1,906,484, 2,749,315, 2,781,321, 2,894,912, 3,879,309, 4,092,259, 4,092,260, 4,096,082 and 4,180,470 teach various fatty acid-isethionate combinations in detergent bars and toilet soaps.

U.S. Pat. Nos. 3,420,857 and 3,420,858 disclose processes for the continuous production of fatty acid esters of hydroxy sulfonates.

U.S. Pat. No. 3,842,119 teaches the synthesis product of halide hydroxypropane sulfonates and $C_{21}$-cycloaliphatic dicarboxylic acid, its preparation and its use as a lime soap dispersant. These products are different from the isethionates and are prepared with a process requiring epichlorohydrin.

Finally, U.S. Pat. No. 4,081,462 teaches $C_{22}$-cycloaliphatic tricarboxylic fatty acid soaps and the method of their preparation.

It is an object of this invention to provide new $C_{22}$-cycloaliphatic tricarboxylic acid based isethionate esters.

Another object of this invention is to provide a process for preparing the $C_{22}$-cycloaliphatic tricarboxylic acid based isethionate esters.

Yet another object of this invention is to provide $C_{22}$-cycloaliphatic tricarboxylic acid based isethionate esters as oil-soluble anionic emulsifier intermediates for emulsifiable concentrates used in agricultural chemical delivery systems.

Other objects, features and advantages will be evident from the following description of the preferred embodiments.

SUMMARY OF THE INVENTION

It has been found that novel anionic emulsifiers are prepared by reacting an ammonium or substituted ammonium methyl isethionate alcohol with $C_{22}$-cycloaliphatic tricarboxylic acid of the formula

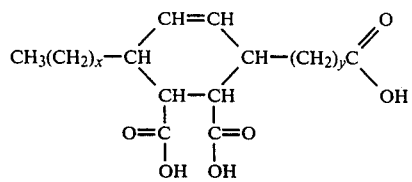

where x and y are integers from 3 to 9, and x and y together equal 12. These oil-soluble emulsifiers are effective in emulsifiable concentrates used in agricultural chemical delivery systems.

The alkali metal or alkaline earth metal isethionate esters may be prepared by further reaction with an organic slurry of an alkali metal or alkaline earth metal hydroxide under reflux conditions until the ammonium or substituted ammonium is distilled out of the reaction system. These compounds also perform as anionic emulsifiers and the oil-soluble emulsifiers (other than lithium or sodium salts) are also effective in emulsifiable concentrates.

DESCRIPTION OF THE PREFERRED EMBODIMENTS

Agricultural chemical emulsifiable concentrates are nonaqueous solutions containing one or more agricultural chemicals, a solvent and from 5% to 10% of a blended emulsifier system. For application, these emulsifiable concentrates are added to spray tanks containing water of varying hardness. The emulsifiers must be soluble in the concentrate and produce a spontaneous stable emulsion when added to the spray tank mix. Typically, these emulsifiers are blends of several nonionic intermediate components and a single anionic component, primarily a petrochemical based fatty derivative. Two types of such anionic components employed in agricultural chemical emulsifiable concentrates are nonylphenol ethoxylate phosphate esters and dodecylbenzene sulfonates. While these are effective emulsifiers, they are relatively expensive.

It has been discovered that isethionate esters derived from $C_{22}$-cycloaliphatic tricarboxylic acid are effective as emulsifiers for agricultural chemical emulsifiable concentrates. Since the $C_{22}$-cycloaliphatic tricarboxylic acid is prepared from linoleic acid containing vegetable oils, such as soybean oil, tall oil, corn oil, cottonseed oil, safflower oil and sunflower oil, the isethionate ester emulsifiers are significantly less expensive than the petroleum based emulsifiers.

The isethionate esters of this invention are produced by esterification of $C_{22}$-cycloaliphatic tricarboxylic acid with the alcohol produced by reacting an alkoxide and a bisulfite. The preferred emulsifier is the ammonium methyl isethionate ester prepared according to the invention process.

The $C_{22}$-cycloaliphatic tricarboxylic acid employed in this invention is described in U.S. Pat. No. 4,081,462 by Powers et al. as

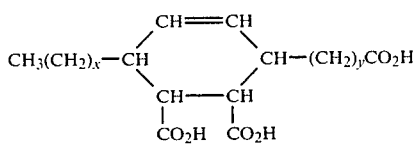

wherein x and y are integers from 3 to 9 and x and y together equal 12. The tricarboxylic acids are produced as the Diels-Alder adducts of fatty acids containing both conjugated and non-conjugated linoleic acids and fumaric acid reacted at from 170° C. to 270° C. in the presence of from 0.01% to 0.50% by weight of iodine.

The methyl isethionate alcohol is produced by reacting ammonium or substituted ammonium bisulfite with an alkoxide such as ethylene oxide or propylene oxide.

The esterification step can follow the synthesis of the $C_{22}$-cycloaliphatic tricarboxylic acid in the same reactor. After the $C_{22}$-tricarboxylic acid is produced according to U.S. Pat. No. 4,081,462, the reaction temperature is reduced to about 145° C. and xylene is added to the reactor. The xylene is allowed to reflux as in an azeotropic distillation. Then a stoichiometric amount of the earlier prepared methyl isethionate alcohol is added to the $C_{22}$-tricarboxylic acid-xylene system, preferably in a controlled manner such that reflux temperature is maintained. While not essential to achieve the desired product, the controlled addition not only allows immediate preparation of the ester, but it also controls foaming in the reaction.

The principle controlling factor in the rate of methyl isethionate solution addition is the temperature of the reaction vessel. It is preferred to keep the reaction temperature up high enough to maintain reflux during the course of the addition to permit a more controlled reaction.

The reaction sequence is as follows:

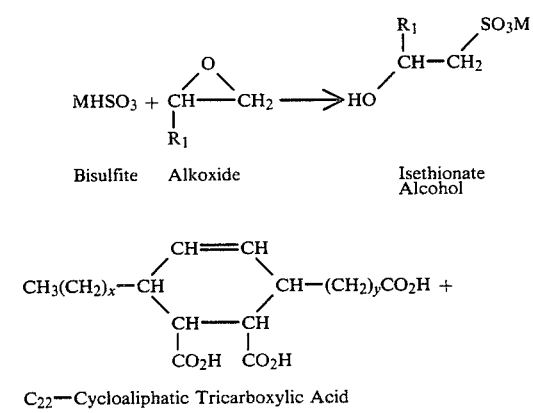

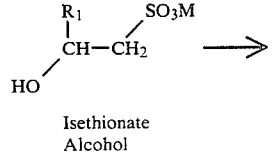

Isethionate Alcohol

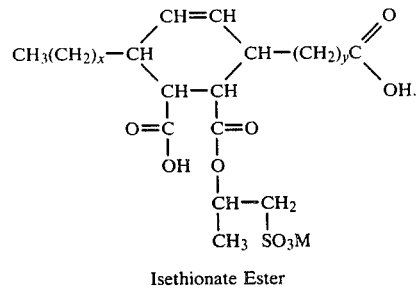

Isethionate Ester

Since the tricarboxylic acid is normally prepared from a mixture of fatty acids in a vegetable oil, monocarboxylic acids will also be present in the esterification reaction, producing the following additional anionic surfactant

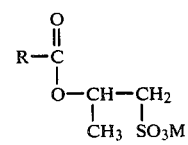

Isethionate Ester

Also, during the esterification reaction, it appears that there is an intermediate formation of highly reactive anhydrides of the ring carboxyls of the $C_{22}$-cycloaliphatic tricarboxylic acid having the following structure

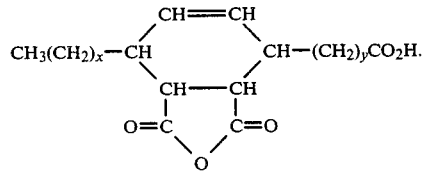

Since the terminal carboxyls on the tricarboxylic acid and monocarboxylic acids are about equally reactive, there is also some bis substitution on the tricarboxylic acid based isethionate ester producing a compound of the following structure

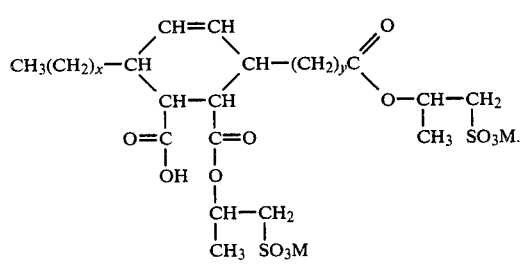

In all of the above equations and formulae x and y are integers from 3 to 9, and x and y together equal 12, R represents $C_9$–$C_{19}$ saturated/unsaturated hydrocarbon radicals and M is a cation selected from the group consisting of an alkali metal, an alkaline earth metal, ammonium or substituted ammonium.

Where M is an alkali metal or alkaline earth metal cation, an additional processing step is employed. After formation of the ammonium or substituted ammonium methyl isethionate ester (see Example 2), a further reaction of the product with an organic slurry of an alkali metal or alkaline earth metal hydroxide at from 145° to 175° C. until the ammonium or substituted ammonium is distilled out of the reaction system which, on a commercial scale, may require at least one hour. After the reaction product cools to about 100° C., appropriate viscosity modifiers may be added as necessary for formulation of an emulsifiable concentrate.

The oil-soluble $C_{22}$-cycloaliphatic tricarboxylic acid derived isethionate ester products of the above described processes have particular utility as emulsifiers for emulsifiable concentrates used in agricultural chemical delivery systems. Though not oil-soluble, the lithium and sodium salts are efficient anionic emulsifiers in aqueous systems.

The manner of preparation and the utility of the invention emulsifiers are shown in the following specific examples.

EXAMPLE 1

Preparation of Ammonium Methyl Isethionate Alcohol Solution

Ammonium bisulfite (2,400 grams of 45% solution in water) was adjusted to pH between 5 and 5.4. (Alternatively, 1,500 grams of a water solution of 70% ammonium bisulfite "as is" may be charged in the one gallon propylene oxide reactor.) The temperature was brought up to 60° C. Propylene oxide (695 grams) was added to the reactor over approximately one hour maintaining reactor pressure of approximately 20 psi. The propylene oxide was allowed to react for approximately 3 hours. The product was removed and the water was distilled off to an approximate 80% concentration of isethionate alcohol. The solids, as determined by moisture balance, was taken as the activity of the ammonium methyl isethionate solution.

EXAMPLE 2

Preparation of Ammonium Methyl Isethionate Ester

A 250 mL three-necked round-bottomed flask with mechanical stirrer, modified Dean Stark trap and nitrogen stream was charged with 80.3 grams $C_{22}$-cycloaliphatic tricarboxylic acid and 47.1 grams xylene. The contents of the flask were brought to reflux at 155° C., and 58.6 grams of 91.1% active ammonium methyl isethionate was dripped in over a 22 minute period. Samples were taken hourly after completion of addition of ammonium methyl isethionate solution. The reaction was conducted for 6.5 hours.

EXAMPLE 3

Preparation of Calcium Methyl Isethionate Ester

A 1,000 ml flask equipped as in Example 2 was charged with 600 grams ammonium methyl isethionate ester solution (prepared as in Example 2). The reaction was stripped under vacuum of 85 grams xylene. A slurry of 20 grams calcium hydroxide in 72 grams Exxon AR 150 (an aromatic solvent) was added. This reaction was continued at 165° C. for two hours. The reaction was cooled to 100° C. and 30 grams butanol and 30 grams propylene glycol were added as viscosity modifiers.

EXAMPLE 4

The calcium and ammonium methyl isethionate esters prepared in Examples 2 and 3 were evaluated in emulsifiable concentrate formulations as emulsifiers for herbicidal systems. The spontaneity (aptitude for forming an immediate emulsion cloud without separation on addition to water) and stability (ability to maintain emulsion and not separate into oil and water phases) of the emulsifiable concentrate formulations are critical for effective application of agricultural chemicals and are primarily dependent upon the emulsifier performance. The following emulsifiable concentrates were formulated for testing:

FORMULATION 1

| | | Weight % |
|---|---|---|
| 1 | Technical Alachlor 95.5% (active) | 44.9 |
| 2 | Monochlorobenzene | 27.2 |
| 3 | Xylene | 18.2 |
| 4 | Ammonium Methyl Isethionate Ester | 3.0 |
| 5 | Calcium Dodecyl Benzene Sulfonate | 1.0 |
| 6 | Nonylphenol-30-EO | 0.6 |
| 7 | Sorbitan Tritallate Ester-20-EO | 0.2 |
| 8 | $C_{21}$-Cycloaliphatic Carboxylic Acid-Polyethylene Glycol Ester | 0.2 |

FORMULATION 2

| (as Formulation 1 except substituting the following for component #4) | Weight % |
|---|---|
| Ammonium Methyl Isethionate Ester | 1.5 |
| Calcium Methyl Isethionate Ester | 1.5 |

FORMULATION 3

| | | Weight % |
|---|---|---|
| 1 | Technical Metolachlor 95% (active) | 91.0 |
| 2 | Exxon AR 150 | 2.0 |
| 3 | Ammonium Methyl Isethionate Ester | 2.1 |
| 4 | Calcium Methyl Isethionate Ester | 2.1 |
| 5 | Calcium Dodecyl Benzene Sulfonate | 0.3 |
| 6 | Nonylphenol-30-EO | 0.3 |
| 7 | $C_{21}$-Cycloaliphatic Carboxylic Acid-Polyethylene Glycol Ester | 2.0 |
| 8 | Sorbitan Tritallate Ester-20-EO | 0.3 |

The spontaneity and stability characteristics of the emulsifiable concentrate formulations were evaluated in this example by visual observation of the emulsion cloud (or "bloom") formed when 5 ml (Formulations 1 and 2) and 4 ml (Formulation 3) of the emulsifiable concentrate is added to 95 and 96 ml, respectively, diluting waters of varying hardness and visual observation of the percent separation of the emulsion after one hour (1% = 1 ml in a 100 ml graduate). On a spontaneity scale of from 1 (little or no bloom) to 10 (thick emulsion cloud with heavy reddish-brown film) an acceptable emulsion concentrate should achieve a value of 7 or above. Also, for Formulations 1 and 2, an acceptable emulsifiable concentrate should exhibit separation residue of less than 4% within one hour at water hardness 1000 and 114 ppm and 2% within one hour at water hardness of 342 ppm. For Formulation 3, an acceptable emulsifiable concentrate should exhibit separation residue of less than 6% within one hour. The results of the evaluation of the above formulations are presented in the following Table:

| | Water Hardness (ppm) | | | | |
|---|---|---|---|---|---|
| | 1000 | 500 | 342 | 114 | 57 |
| Formulation 1 | | | | | |
| Residue % | 1 | — | 0.5 | 2.5 | — |
| Bloom | 8 | — | 7 | 6 | — |
| Formulation 2 | | | | | |
| Residue % | 0 | — | 0 | 0 | — |
| Bloom | 8 | — | 8 | 7 | — |
| Formulation 3* | | | | | |
| Residue % | — | 2 | — | — | 3 |

*The manufacturer of metolachlor does not specify an acceptable bloom criteria.

The data in the above Table shows all formulations tested perform as emulsifiable concentrate emulsifiers. Formulation 2, comprising the combination of ammonium and calcium methyl isethionate esters, is particularly efficient in this application.

While the invention has been described and illustrated herein by references to various specific materials, procedures and examples, it is understood that the invention is not restricted to the particular materials, combinations of materials, and procedures selected for that purpose. Numerous variations of such details can be employed, as will be appreciated by those skilled in the art.

What is claimed is:

1. An anionic emulsifier comprising at least one compound of the group selected from the following formulae:

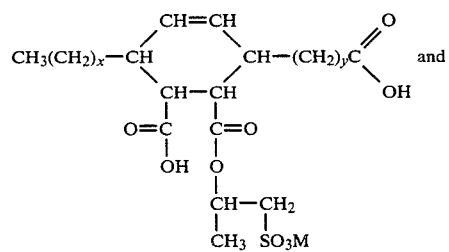 and

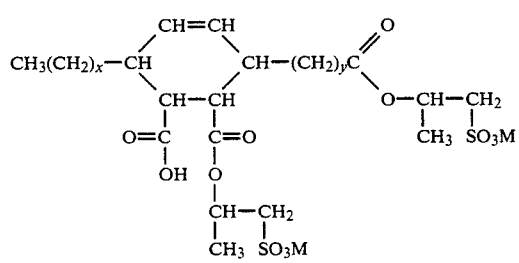

where x and y are integers from 3 to 9, and x and y together equal 12, and M is a cation selected from the group consisting of alkali metals, alkaline earth metals, ammonium or substituted ammonium.

2. A compound of the general formula

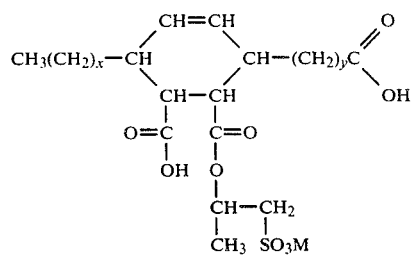

where x and y are integers from 3 to 9, and x and y together equal 12, and M is a cation selected from the group consisting of alkali metals, alkaline earth metals, ammonium or substituted ammonium.

3. A compound of the general formula

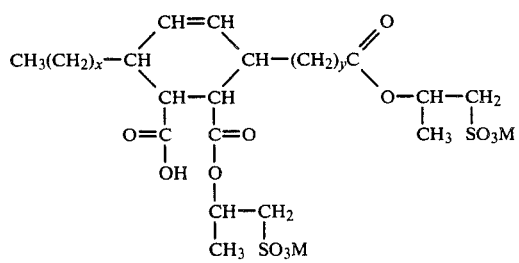

where x and y are integers from 3 to 9, and x and y together equal 12, and M is a cation selected from the group consisting of alkali metals, alkaline earth metals, ammonium and substituted ammonium.

4. An emulsifiable concentrate formulation for agricultural chemical delivery systems comprising an agricultural chemical, a solvent and, from 5% to 10% of an oil-soluble, anionic emulsifier comprising at least one compound selected from the group consisting of the following formulae:

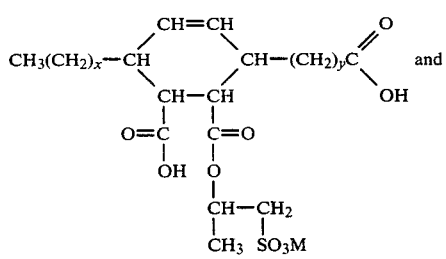 and

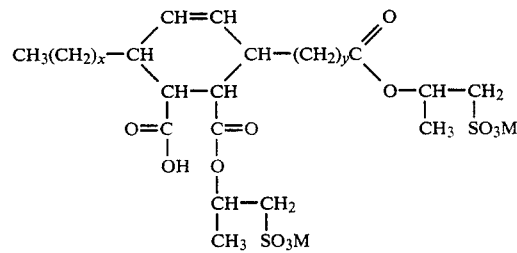

where x and y are integers from 3 to 9, and x and y together equal 12, and M is a cation selected from the group consisting of alkaline earth metals, the alkali metals $K^+$, $Rb^+$ and $Cs^+$, ammonium and substituted ammonium.

5. In a process for preparing an isethionate ester which comprises reacting an isethionate alcohol with a fatty acid, the improvement comprising reacting ammonium or substituted ammonium methyl isethionate alcohol with $C_{22}$-cycloaliphatic tricarboxylic acid of the formula

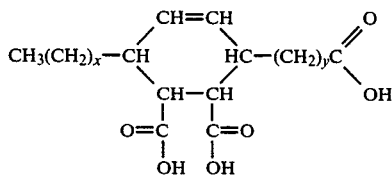

where x and y are integers from 3 to 9, and x and y together equal 12, said reaction producing an intermediate formation of anhydrides of the ring carboxyls of said $C_{22}$-cycloaliphatic tricarboxylic acid and said reaction further comprising the steps of
(a) heating said $C_{22}$-cycloaliphatic tricarboxylic acid and xylene to produce reflux in an inert atmosphere,
(b) adding a stoichiometric amount of said ammonium or substituted ammonium methyl isethionate alcohol, based on said $C_{22}$-cycloaliphatic tricarboxylic acid, at a controlled rate over 0.25 to 0.75 hour, and
(c) continuing the reaction under reflux conditions for up to 12 hours.

6. The process of claim 5 wherein the isethionate ester reaction product is further reacted with an organic slurry of a hydroxide selected from the group consisting of alkali metal hydroxides and alkaline earth metal hydroxides under reflux conditions of temperature and pressure until the ammonium or substituted ammonium is removed.

7. The process of claim 5 or 6 wherein the $C_{22}$-cycloaliphatic tricarboxylic acid is provided as a mixture of fatty acids comprised of at least 5% as $C_{22}$-cycloaliphatic tricarboxylic acid and at most 95% as a mixture of aliphatic hydrocarbons having from 8 to 20 carbon atoms and including unsubstituted, saturated and unsaturated straight-chain fatty acids.

8. The process of claim 7 wherein the aliphatic hydrocarbons are derived from at least one member of the group consisting of soybean oil, corn oil, cottonseed oil, safflower oil, sunflower oil, and tall oil.

9. The process of claim 8 wherein the aliphatic hydrocarbons are derived from tall oil.

10. The process of claim 9 wherein the mixture of fatty acids consists essentially of approximately 30% $C_{22}$-cycloaliphatic tricarboxylic acid and approximately 70% of a majority of monounsaturated fatty acids and a minority of palmitic acid, stearic acid and linoleic acid.

11. The process of claim 5 wherein the inert atmosphere is provided by a vacuum or a nitrogen gas or carbon dioxide gas sparge.

12. The process of claim 5 or 6 wherein the methyl isethionate alcohol is provided as the ammonium salt.

* * * * *